(12) United States Patent
Lin et al.

(10) Patent No.: US 10,618,891 B2
(45) Date of Patent: Apr. 14, 2020

(54) SUVOREXANT INTERMEDIATE AND PREPARATION METHOD THEREOF

(71) Applicants: Zhejiang Huahai Pharmaceutical Co., Ltd., Zhejiang (CN); Shanghai Aobo Pharmtech, Inc., Ltd., Shanghai (CN)

(72) Inventors: Jianping Lin, Shanghai (CN); Xiaowen Guo, Shanghai (CN); Xiaofei Gao, Shanghai (CN); Chao Huang, Shanghai (CN); Yuanbing Guo, Shanghai (CN); Anping Tao, Shanghai (CN); Luning Huang, Shanghai (CN); Hong Gu, Shanghai (CN)

(73) Assignees: Zhejiang Huahai Pharmaceutical Co., Ltd., Zhejiang (CN); Shanghai Aobo Pharmtech, Inc., Ltd., Shanghai (CN)

( * ) Notice: Subject to any disclaimer, the term of this patent is extended or adjusted under 35 U.S.C. 154(b) by 0 days.

(21) Appl. No.: 16/073,929

(22) PCT Filed: Jan. 25, 2017

(86) PCT No.: PCT/CN2017/072624
§ 371 (c)(1),
(2) Date: Jul. 30, 2018

(87) PCT Pub. No.: WO2017/133620
PCT Pub. Date: Aug. 10, 2017

(65) Prior Publication Data
US 2019/0040052 A1    Feb. 7, 2019

(30) Foreign Application Priority Data
Feb. 1, 2016   (CN) .......................... 2016 1 0070443

(51) Int. Cl.
*C07D 413/14*   (2006.01)
*C07D 413/04*   (2006.01)
(Continued)

(52) U.S. Cl.
CPC .......... *C07D 413/14* (2013.01); *C07C 269/06* (2013.01); *C07C 271/22* (2013.01); *C07D 243/08* (2013.01); *C07D 413/04* (2013.01)

(58) Field of Classification Search
CPC ........................... C07D 413/14; C07D 413/04
See application file for complete search history.

(56) References Cited

FOREIGN PATENT DOCUMENTS

WO    WO 2008/069997 A1    6/2008
WO    WO 2012/148533 A1    11/2012
(Continued)

OTHER PUBLICATIONS

Yin Chen et al., Facile synthesis of suvorexant, an orexin receptor antagonist via a chiral diazepane intermediate; Chinese Chemical letters: 26 (2015), 103-107.*

(Continued)

Primary Examiner — Alexander R Pagano
Assistant Examiner — Ebenezer O Sackey
(74) Attorney, Agent, or Firm — Wolf, Greenfield & Sacks, P.C.

(57) ABSTRACT

The present invention relates to a synthesis process of suvorexant, novel compounds represented by formulas II, III, IV or V, or salts thereof for preparing suvorexant, and a method for preparing the intermediates. The preparation method uses a chiral starting material to synthesize chiral compounds represented by formulas II, III, IV or V, the compounds obtained being used for synthesizing the suvorexant. The preparation method has the advantages of simple operation, low cost, mild reaction conditions, simple post-treatment, easy to purify, high yield, high ee value for the product, and easy to industrialize. In the reaction route shown, R represents benzyl, allyl or 1-phenethyl, or optionally substituted benzyl at the 2 position to 6 position, such as 4-methoxybenzyl, 4-nitrobenzyl, 2-methylbenzyl, 4-chlorobenzyl or 3-fluorobenzyl.

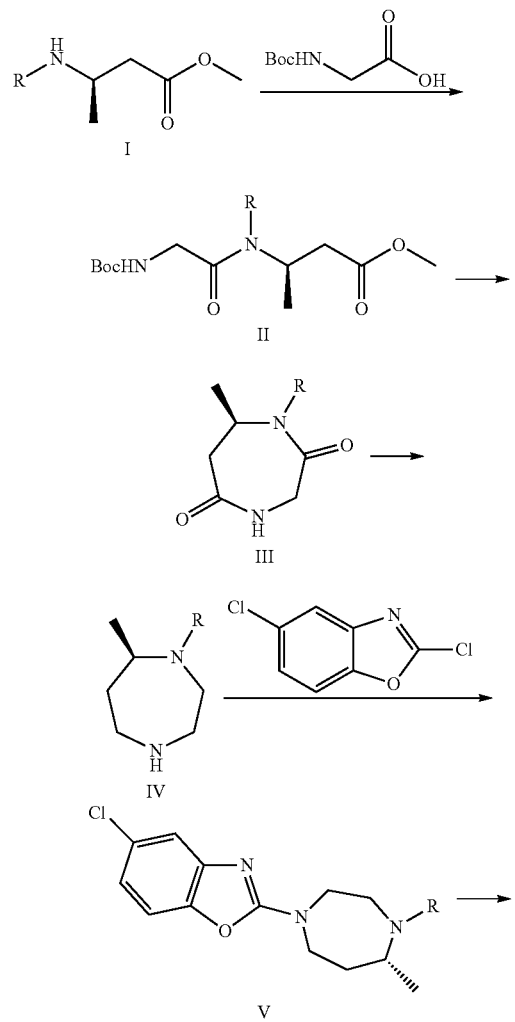

(Continued)

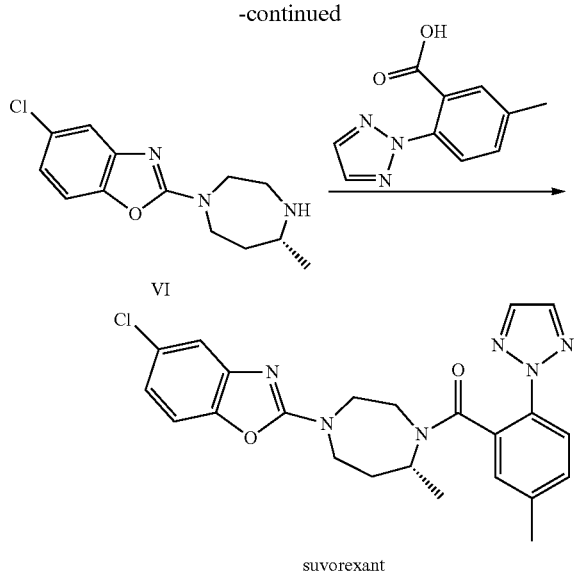

suvorexant

17 Claims, No Drawings

(51) Int. Cl.
*C07D 243/08* (2006.01)
*C07C 269/06* (2006.01)
*C07C 271/22* (2006.01)

(56) References Cited

FOREIGN PATENT DOCUMENTS

| WO | WO 2013/169610 A1 | 11/2013 |
|---|---|---|
| WO | WO 2016/020404 A1 | 2/2016 |
| WO | WO 2016/020405 A1 | 2/2016 |
| WO | WO 2016/020406 A1 | 2/2016 |

OTHER PUBLICATIONS

Masakazu Hatano et al., Assessment of Switching to Suvorexant verses the use of Add-on Suvorexant in combination with Benzodiazepine Receptor Agonists in Insomnia Patients: A retrospective Study, Clinical Psychoparmacol Neuroscience, May 2018, 16(2), 184-189.*

International Search Report and Written Opinion dated May 2, 2017 in connection with PCT/CN2017/072624.

Chen et al., Facile synthesis of suvorexant, an orexin receptor antagonist, via a chiral diazepane intermediate. Chin Chem Lett. Jan. 31, 2015; 26(1):103-107.

Strotman et al., Reaction development and mechanistic study of a ruthenium catalyzed intramolecular asymmetric reductive amination en route to the dual orexin inhibitor Suvorexant (MK-4305). J Am Chem Soc. May 2, 2011; 133(21):8362-8371.

Ukrorgsyntez Ltd., "RN 1343179-52-1", STN Registry, Nov. 9, 2011.

Ukrorgsyntez Ltd., "RN 1344251-09-7", STN Registry, Nov. 9, 2011.

* cited by examiner

SUVOREXANT INTERMEDIATE AND PREPARATION METHOD THEREOF

CROSS REFERENCE TO RELATED APPLICATIONS

The present application is the National Phase Under 35 U.S.C. § 371 of PCT International Application No. PCT/CN2017/072624, filed Jan. 25, 2017, which claims the priority of the Chinese application of No. 201610070443.7, titled "Suvorexant intermediate and preparation method thereof", filed with State Intellectual Property Office of the P.R.C on Feb. 1, 2016, the contents of which are is incorporated into the present application by reference in their entirety.

The present application claims the priority of the Chinese application of No. 201610070443.7, titled "Suvorexant intermediate and preparation method thereof", filed with State Intellectual Property Office of the P.R.C on Feb. 1, 2016, the content of which is incorporated into the present application by reference in its entirety.

TECHNICAL FIELD

The present invention relates to a technical field of pharmaceutical synthesis, and provides a synthesis process for suvorexant, novel compounds represented by formulas II, III, IV or V, or salts thereof for preparing suvorexant, and a method for preparing the intermediates.

BACKGROUND

Orexins are neuropeptides that are involved in the regulation of the sleep-wake cycle and play an important role in maintaining human awake. Suvorexant is an Orexins receptor antagonist and improves the sleep of patients by blocking the transmission of messages by Orexins. The US Food and Drug Administration (FDA) approved the launch of Merck's new insomnia drug suvorexant (Trade name: Belsomra) on Aug. 13, 2014.

The synthetic route of this compound is reported in the following documents.

(1) The synthetic route reported in US2008/132490 is as follows.

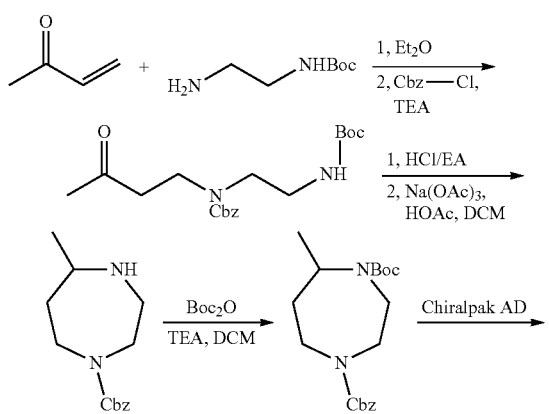

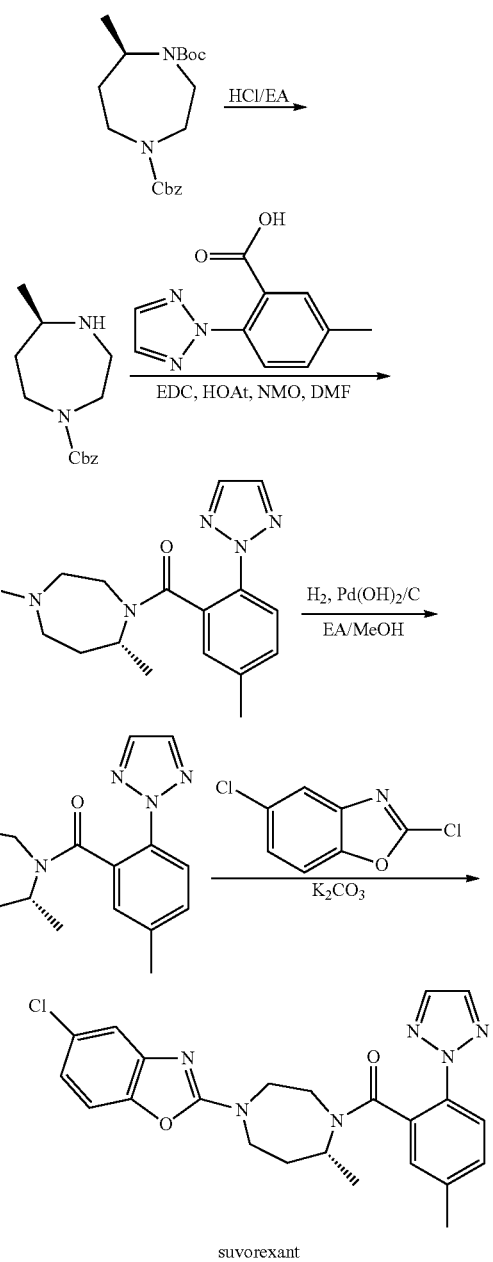

(2) The synthetic route reported in *Org. Process Res. Dev.* 2011, 15, 367-375 is as follows.

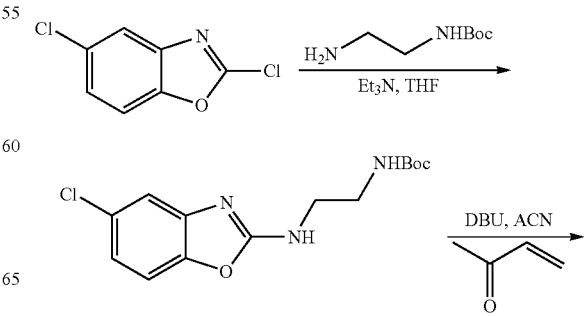

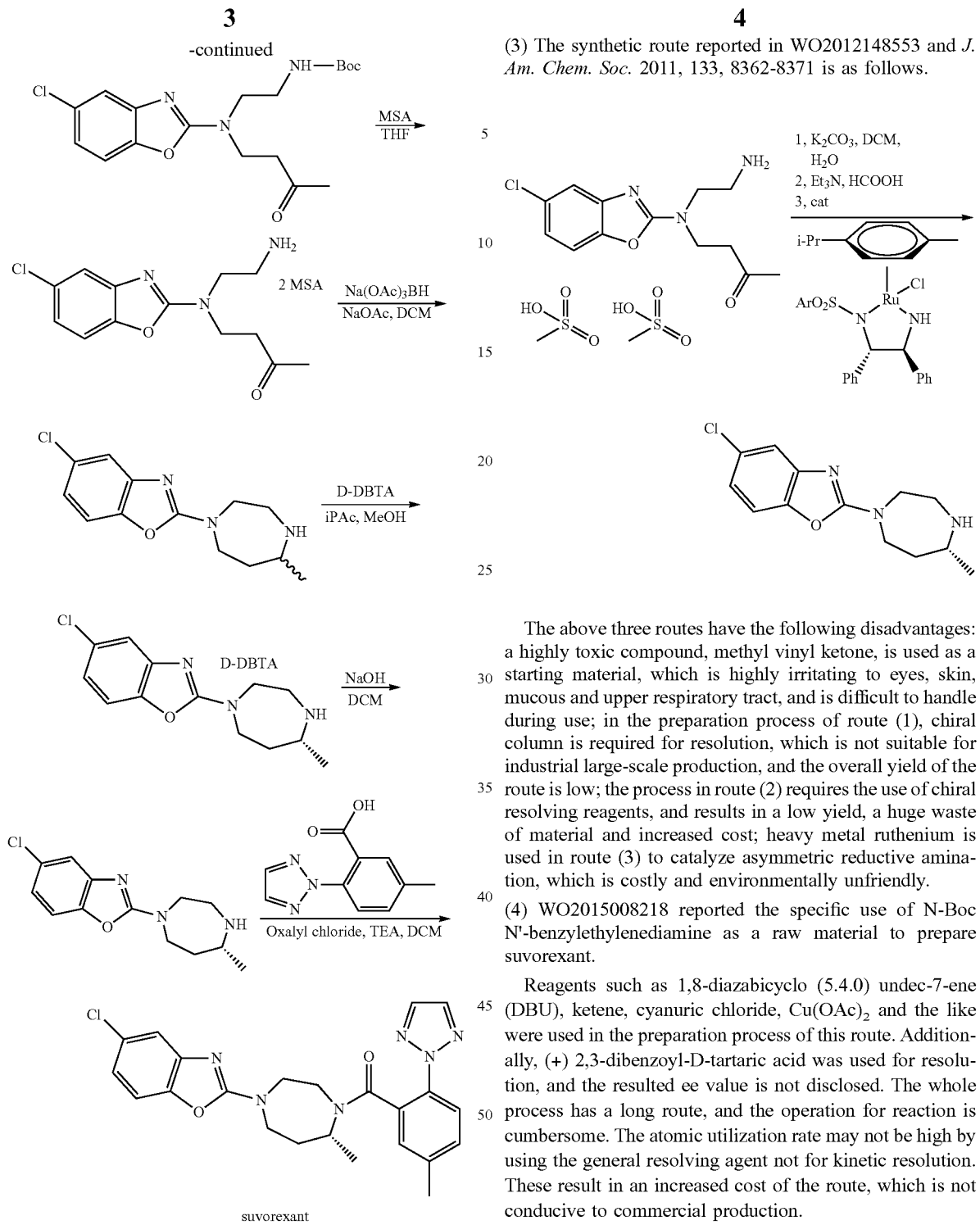

(3) The synthetic route reported in WO2012148553 and *J. Am. Chem. Soc.* 2011, 133, 8362-8371 is as follows.

The above three routes have the following disadvantages: a highly toxic compound, methyl vinyl ketone, is used as a starting material, which is highly irritating to eyes, skin, mucous and upper respiratory tract, and is difficult to handle during use; in the preparation process of route (1), chiral column is required for resolution, which is not suitable for industrial large-scale production, and the overall yield of the route is low; the process in route (2) requires the use of chiral resolving reagents, and results in a low yield, a huge waste of material and increased cost; heavy metal ruthenium is used in route (3) to catalyze asymmetric reductive amination, which is costly and environmentally unfriendly.

(4) WO2015008218 reported the specific use of N-Boc N'-benzylethylenediamine as a raw material to prepare suvorexant.

Reagents such as 1,8-diazabicyclo (5.4.0) undec-7-ene (DBU), ketene, cyanuric chloride, Cu(OAc)₂ and the like were used in the preparation process of this route. Additionally, (+) 2,3-dibenzoyl-D-tartaric acid was used for resolution, and the resulted ee value is not disclosed. The whole process has a long route, and the operation for reaction is cumbersome. The atomic utilization rate may not be high by using the general resolving agent not for kinetic resolution. These result in an increased cost of the route, which is not conducive to commercial production.

The specific reaction formula is as follows:

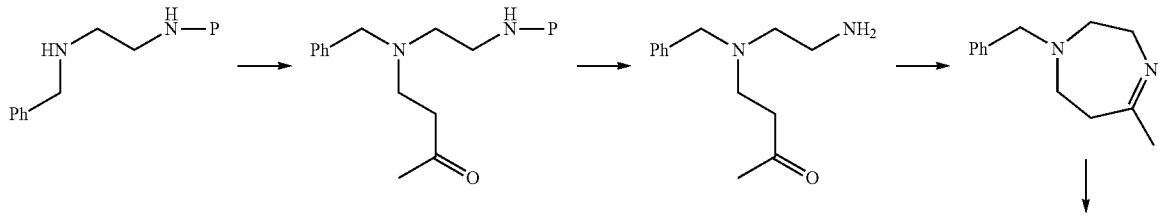

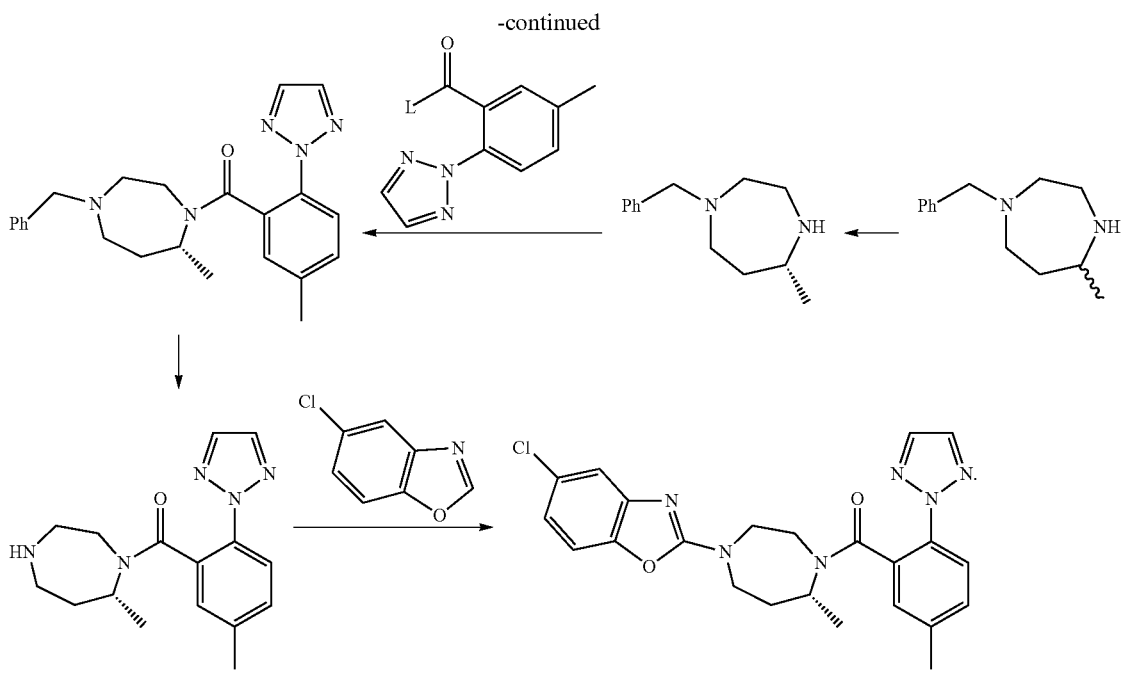

It can be seen that the development of new methods for synthesizing suvorexant and its intermediate compounds to overcome the shortcomings of the prior art is of great significance.

SUMMARY OF THE INVENTION

The present invention relates to a synthesis process of suvorexant, novel compounds represented by formulas II, III, IV or V, or salts thereof for preparing suvorexant, and a method for preparing the intermediates.

The complete synthetic route is as follows.

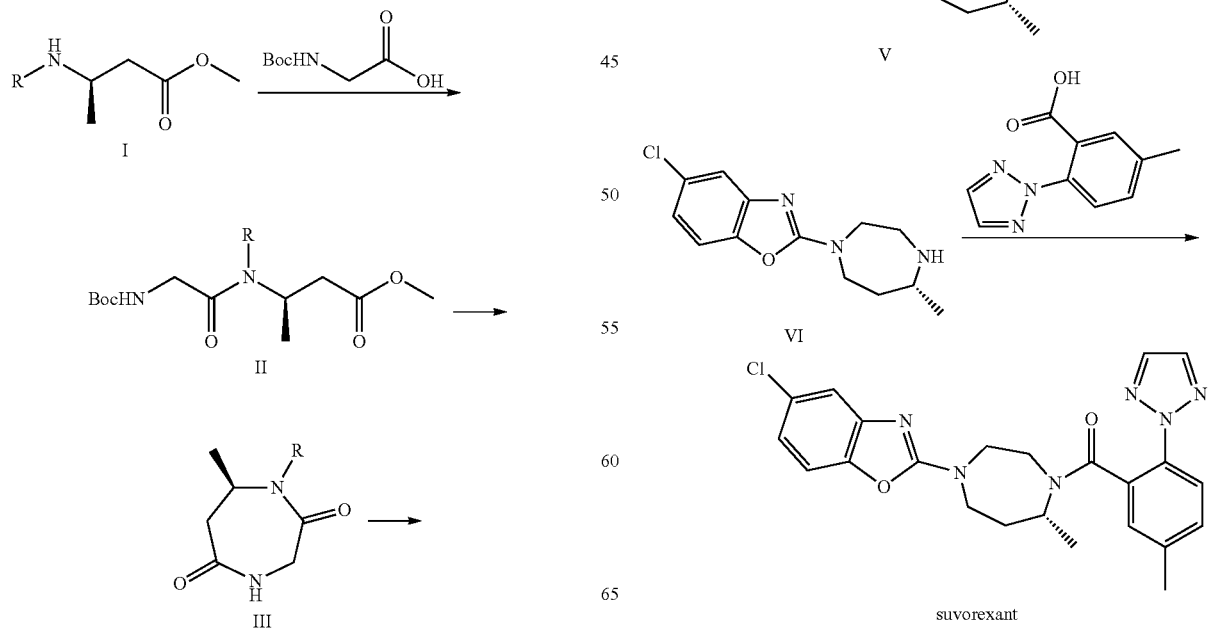

Route for experiments: subjecting the compound of formula I and amino acid protected by t-butoxycarbonyl(Boc) to a condensation agent in an alkaline condition to obtain a compound of formula II; deprotecting the Boc from the compound of formula II in an acidic condition, and then cyclizing the resultant in an alkaline condition to give a compound of formula III; reducing the compound of formula III by hydrogenation to give a compound of formula IV; reacting the compound of formula IV with 2,5-dichlorobenzoxazole in an alkaline condition to give a compound of formula V; deprotecting R group from the compound of formula V in the presence of a catalyst, to give the compound of formula VI; and reacting the compound of formula VI with 5-methyl-2-(2H-1,2,3-triazol-2-yl)benzoic acid in an alkaline condition by a condensation agent to give suvorexant.

Particularly, preferred technical solutions are as follows.

The present invention provides a method for preparing a compound of formula II, comprising:

subjecting a compound of formula I and glycine protected by Boc to a condensation reaction in an organic solvent under an alkaline condition and a condensation agent, to obtain the compound of formula II;

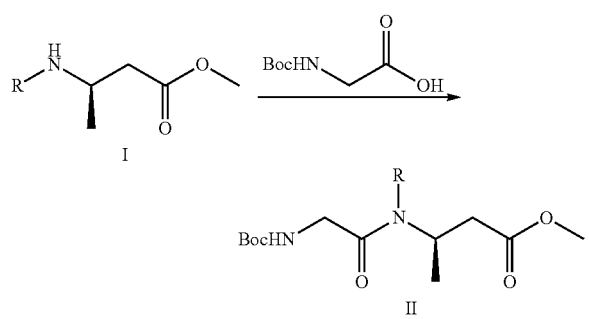

R represents benzyl, allyl, 1-phenethyl, or arbitrarily substituted benzyl at the 2 position to 6 position, such as 4-methoxybenzyl, 4-nitrobenzyl, 2-methylbenzyl, 4-chlorobenzyl, or 3-fluorobenzyl;

wherein the organic solvent used in the condensation reaction for preparing the compound of formula II is selected from the group consisting of dichloromethane, tetrahydrofuran and N,N-dimethylformamide, preferably N,N-dimethylformamide;

wherein the alkali used in the condensation reaction for preparing the compound of formula II is selected from the group consisting of triethylamine, 1,8-diazabicyclo (5.4.0) undec-7-ene, 4-dimethylaminopyridine (DMAP), N-methylmorpholine, N-methylpiperazine, piperidine, sodium hydrogencarbonate, potassium carbonate and sodium hydride, preferably triethylamine or N-methylmorpholine;

wherein the condensation agent used in the condensation reaction for preparing the compound of formula II is selected from the group consisting of 1-ethyl-(3-dimethyl aminopropyl) carbodiimide hydrochloride, N,N'-carbonyldiimidazole, dicyclohexylcarbodiimide, 1-hydroxybenzotriazole, and 1-hydroxy-7-azobenzotriazole, preferably a combination of 1-hydroxybenzotriazole and 1-ethyl-(3-dimethylaminopropyl) carbodiimide hydrochloride.

The present invention provides a method for preparing a compound of formula III, comprising:

deprotecting Boc from the compound of formula II in the presence of an acid in an organic solvent, to give a corresponding amine or the salt thereof; and then subjecting the corresponding amine or the salt thereof to a cyclization reaction in the presence of an alkali to give a compound of formula III;

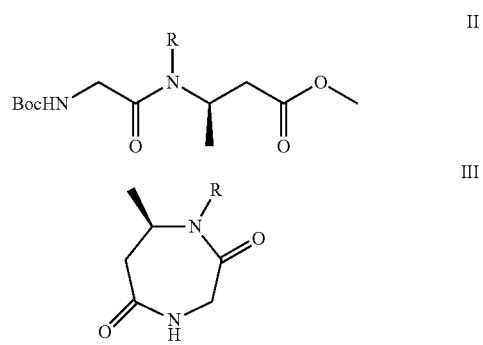

R represents benzyl, allyl, 1-phenethyl, or arbitrarily substituted benzyl at the 2 position to 6 position, such as 4-methoxybenzyl, 4-nitrobenzyl, 2-methylbenzyl, 4-chlorobenzyl, or 3-fluorobenzyl;

wherein the organic solvent used in the reaction of deprotecting the Boc from the compound of formula II is selected from the group consisting of ethyl acetate, dichloromethane, N,N-dimethylformamide, acetonitrile, toluene, methanol and ethanol;

wherein the acid used in the reaction of deprotecting the Boc from the compound of formula II is selected from the group consisting of HCl, trifluoroacetic acid and the like;

wherein the alkali in the reaction of deprotecting the Boc from the compound of formula II is selected from the group consisting of magnesium alkoxide, sodium alkoxide, sodium hydride, sodium hydrogencarbonate, sodium carbonate, potassium carbonate, sodium borohydride, potassium t-butoxide, and triethylamine.

The present invention provides a method for preparing a compound of formula IV, comprising:

subjecting a compound of formula III to a reduction reaction in the presence of a reducing agent, to give the compound of formula IV, or a salt thereof,

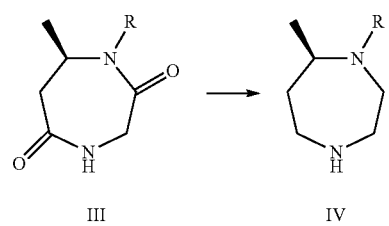

R represents benzyl, allyl, 1-phenethyl, or arbitrarily substituted benzyl at the 2 position to 6 position, such as 4-methoxybenzyl, 4-nitrobenzyl, 2-methylbenzyl, 4-chlorobenzyl, or 3-fluorobenzyl;

wherein the solvent used in the reduction reaction is selected from the group consisting of dichloromethane and tetrahydrofuran;

wherein the reducing agent used in the reduction reaction is selected from the group consisting of borane, sodium borohydride, lithium borohydride, sodium cyanoborohydride, lithium aluminum hydride, and sodium hydride.

The present invention provides a method for preparing a compound of formula V, comprising:

subjecting a compound of formula IV and 2,5-dichlorobenzoxazole to a C—N coupling reaction in the presence of an alkali, to give the compound of formula V or a salt thereof,

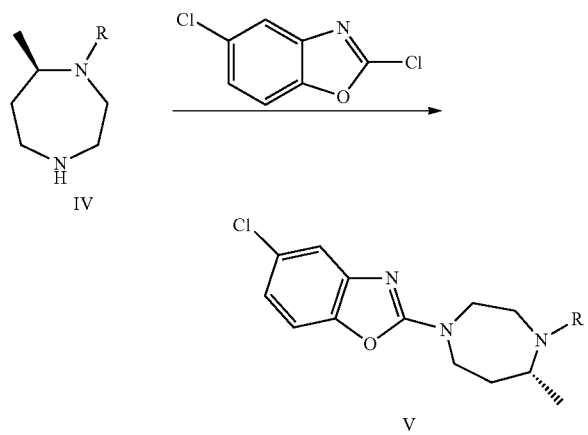

R represents benzyl, allyl, 1-phenethyl or arbitrarily substituted benzyl at the 2 position to 6 position, such as 4-methoxybenzyl, 4-nitrobenzyl, 2-methylbenzyl, 4-chlorobenzyl, or 3-fluorobenzyl;

wherein the solvent used in the C—N coupling reaction is selected from the group consisting of N,N-dimethylformamide, toluene, tetrahydrofuran and acetonitrile;

wherein the alkali used in the C—N coupling reaction is selected from the group consisting of triethylamine, N-methylmorpholine, piperidine, N-methylpiperazine, sodium hydrogencarbonate, potassium hydrogencarbonate, potassium carbonate, and sodium hydride.

The present invention provides a method for preparing a compound of formula VI, comprising:

deprotecting a protecting group R from a compound of formula V via a deprotection reaction in the presence of a catalyst in an organic solvent,

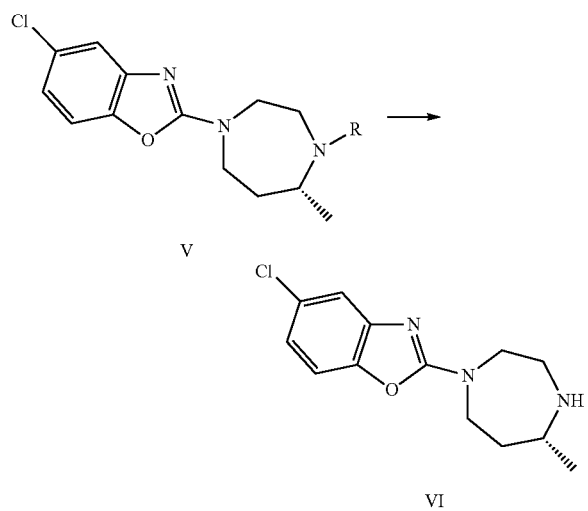

R represents benzyl, allyl, 1-phenethyl, or arbitrarily substituted benzyl at the 2 position to 6 position, such as 4-methoxybenzyl, 4-nitrobenzyl, 2-methylbenzyl, 4-chlorobenzyl, or 3-fluorobenzyl;

wherein the organic solvent used in the deprotection reaction is selected from the group consisting of a $C_1$-$C_4$ lower alcohol and a halohydrocarbon, preferably methanol, ethanol or 1,2-dichloroethane;

wherein the catalyst used in the deprotection reaction is selected from the group consisting of a chloroformate catalyst and a palladium catalyst, wherein the chloroformate catalyst is preferably chloroethyl chloroformate, and the palladium catalyst is preferably Pd/C, Pd(OH)$_2$/C or PdCl$_2$/C.

The present invention further provides a method for preparing suvorexant from a compound of formula VI, comprising:

subjecting the compound of formula VI and 5-methyl-2-(2H-1,2,3-triazol-2-yl)benzoic acid to a condensation reaction in the presence of a condensation agent, an alkali and an aprotic solvent, shown as the following reaction formula:

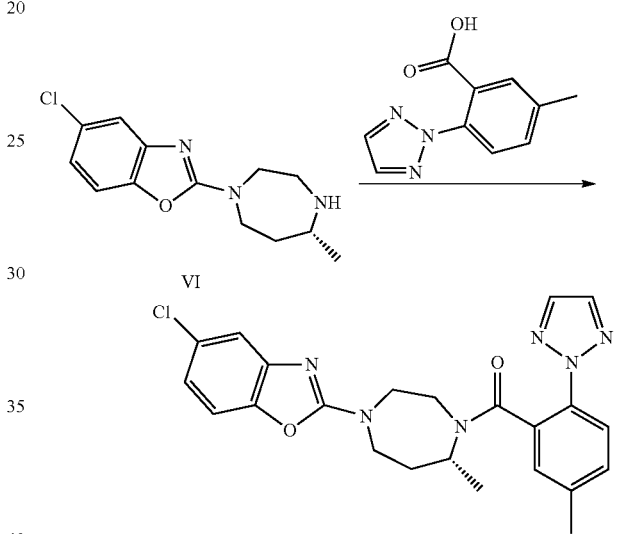

wherein the aprotic solvent used in the condensation reaction for preparing suvorexant is selected from the group consisting of acetonitrile, tetrahydrofuran, toluene, dichloromethane, N,N-dimethylformamide and the like, preferably N,N-dimethylformamide;

wherein the condensation agent used in the condensation reaction for preparing suvorexant is selected from the group consisting of 1-ethyl-3-(3-dimethylaminopropyl) carbodiimide hydrochloride, N, N-diisopropylcarbodiimide, N,N'-carbonyldiimidazole, dicyclohexylcarbodiimide, 1-hydroxybenzotriazole, and 1-hydroxy-7-azobenzotriazole, preferably a combination of 1-hydroxybenzotriazole and 1-ethyl-(3-dimethylaminopropyl) carbodiimide hydrochloride;

wherein the alkali used in the condensation reaction for preparing suvorexant is selected from the group consisting of triethylamine, 1,8-diazabicyclo (5.4.0) undec-7-ene (DBU), 4-dimethylaminopyridine(DMAP), N-methylmorpholine or N-methylpiperazine or piperidine, preferably triethyl amine or N-methylmorpholine.

In another aspect, the present invention further relates to four novel compounds for preparing suvorexant, i.e. a compound of formula II, a compound of formula III, a compound of formula IV, and a compound of formula V, or salts thereof:

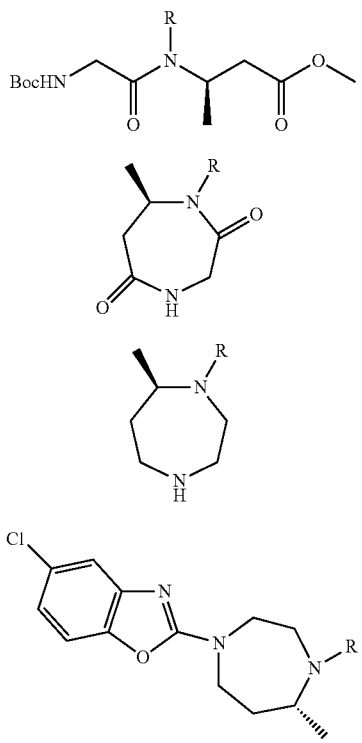

R represents benzyl, allyl, 1-phenethyl, or arbitrarily substituted benzyl at the 2 position to 6 position, such as 4-methoxybenzyl, 4-nitrobenzyl, 2-methylbenzyl, 4-chlorobenzyl, or 3-fluorobenzyl.

The compound of formula II preferably is (R)-methyl 3-(N-benzyl-2-((t-butyloxycarboryl) amino) acetamido) butyrate;

the compound of formula III preferably is (R)-1-benzyl-7-methyl-1,4-diazepane-2,5-dione;

the compound of formula IV preferably is (R)-1-benzyl-7-methyl-1,4-diazepane; and the compound of formula V preferably is 5-chloro-2-[(5R)-hexahydro-4-benzyl-5-methyl-1H-1,4-diazepin-1-yl]benzoxazole.

The present invention has beneficial technical effects as follows: 5-methyl-2-(2H-1,2,3-triazol-2-yl)benzoic acid, which is relatively expensive, is designed for the final step in the present invention, and thus the atomic utilization rate of the compound is improved and the production cost is reduced greatly, when compared with the prior art; meanwhile, methyl vinyl ketone or ketene, a flammable compound with high toxicity, is avoided to construct the diazepane backbone, and provides a suvorexant intermediate with a desired configuration through a chiral starting material; the reaction is performed under mild conditions, and has the advantages of simple post-treatment, high yield and high ee value of the product, and easy to industrialize.

EMBODIMENTS

The invention is further illustrated by the following examples, which are not intended to limit the invention.

Example 1

Synthesis of (R)-methyl 3-(N-benzyl-2-((t-butyloxycarboryl) amino) acetamido) butyrate

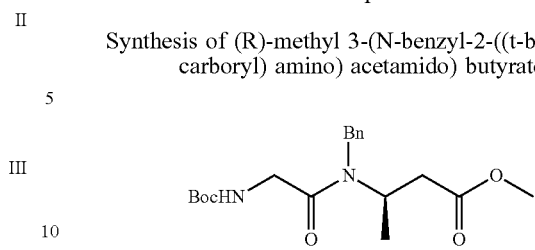

(R)-methyl 3-(benzylamino)-butyrate (40 mmol) was added into a flask, dissolved with 80 ml anhydrous DMF; the system was cooled to 0-5° C., added with 1-hydroxybenzotriazole (48 mmol), 1-ethyl-(3-dimethylaminopropyl) carbodiimide hydrochloride (48 mmol), N-methylmorpholine (100 mmol) and N-(t-butoxycarbonyl) aminoacetic acid (44 mmol) with stirring, then reacted at room temperature for 6 h, and added with 10 mass % citric acid solution. The aqueous phase separated was extracted with ethyl acetate. All organic phase was washed with saturated sodium bicarbonate solution followed by saturated brine, dried over anhydrous sodium sulfate and filtered. The solvent was evaporated to dryness, and the residue was recrystallized with ethyl acetate and petroleum ether to obtain (R)-methyl 3-(N-benzyl-2-((t-butoxycarbonyl) amino) acetamido) butyrate with a yield of 93%. $^1$H NMR (400 MHz, CDCl$_3$) δ 7.35 (t, J=7.3 Hz, 1H), 7.31-7.11 (m, 4H), 5.56 (d, J=38.0 Hz, 1H), 4.63-4.31 (m, 3H), 4.23-4.07 (m, 1H), 3.97-3.83 (m, 1H), 3.57 (d, J=53.8 Hz, 3H), 2.80 (dd, J=15.6, 7.4 Hz, 1H), 2.60-2.47 (m, 1H), 1.44 (d, J=16.0 Hz, 9H), 1.26-1.21 (m, 3H); MS (ESI) m/z 365.20 ([M+H]$^+$).

(R)-methyl 3-(N-allyl-2-((t-butoxycarbonyl)amino)acetamido) butyrate, (R)-methyl 3-(N-(1-phenylethyl)-2-((t-butyloxycarboryl)amino)acetamido) butyrate, (R)-methyl 3-(N-(4-methoxybenzyl)-2-((t-butyloxycarboryl)amino)acetamido) butyrate, (R)-methyl 3-(N-(4-chlorobenzyl)-2-((t-butyloxycarboryl)amino)acetamido) butyrate, (R)-methyl 3-(N-(3-fluorobenzyl)-2-((t-butyloxycarboryl)amino)acetamido) butyrate, (R)-methyl 3-(N-(2-methylbenzyl)-2-((t-butyloxycarboryl)amino)acetamido) butyrate, (R)-methyl 3-(N-(4-nitrobenzyl)-2-((t-butyloxycarboryl)amino)acetamido) butyrate were prepared from (R)-methyl 3-(allylamino)-butyrate (40 mmol), (R)-methyl 3-(1-phenylethylamino)-butyrate (40 mmol), (R)-methyl 3-(4-methoxybenzylamino)-butyrate (40 mmol), (R)-methyl 3-(4-chlorobenzylamino)-butyrate (40 mmol), (R)-methyl 3-(3-fluorobenzylamino)-butyrate (40 mmol), (R)-methyl 3-(2-methylphenylamino)-butyrate (40 mmol), (R)-methyl 3-(4-nitrophenylamino)-butyrate (40 mmol), respectively, in the same manner as the above-mentioned method of this example.

Example 2

Synthesis of (R)-1-benzyl-7-methyl-1,4-diazepane-2,5-dione

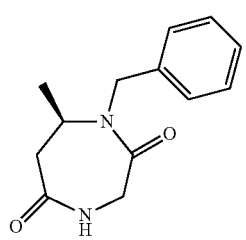 [SMILES: C[C@@H]1CC(=O)NCC(=O)N1Cc1ccccc1]

(R)-methyl 3-(N-benzyl-2-((t-butyloxycarboryl)amino) acetamido) butyrate (10 mmol) was added into a flask, dissolved with 10 ml methanol, added with 40 ml of 30 mass % of solution of HCl in methanol, and reacted at 50° C. for 6 h. The mixture was concentrated to dry under reduced pressure to give yellow oil. The yellow oil was dissolved in 50 ml anhydrous toluene, added with potassium carbonate (20 mmol), and reacted at 110° C. overnight. After being cooled to room temperature, the system was quenched by adding saturated aqueous solution of ammonium chloride, and extracted with dichloromethane. The organic phase separated was washed with saturated brine, and dried with anhydrous sodium sulfate and with rotary evaporation to give white solid with a yield of 92%. $^1$H NMR (400 MHz, CDCl$_3$) δ 7.40-7.17 (m, 5H), 6.24 (s, 1H), 5.24 (d, J=15.1 Hz, 1H), 4.25 (dd, J=17.5, 3.0 Hz, 1H), 4.09 (d, J=15.1 Hz, 1H), 4.00 (dd, J=17.5, 7.1 Hz, 1H), 3.72 (td, J=6.6, 3.4 Hz, 1H), 3.02 (dd, J=15.0, 3.2 Hz, 1H), 2.50 (m, 1H), 1.38 (d, J=6.6 Hz, 3H); MS (ESI) m/z 233.10 ([M+H]$^+$).

Example 3

Synthesis of (R)-1-allyl-7-methyl-1,4-diazepane-2,5-dione

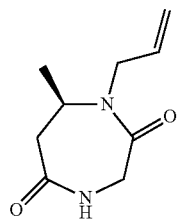

(R)-methyl 3-(N-allyl-2-((t-butyloxycarboryl)amino)acetamido) butyrate (10 mmol) was added into a flask, dissolved with 10 ml methanol; added with 40 ml of 30 mass % of solution of HCl in methanol, and reacted at 50° C. for 6 h. The mixture was concentrated to dry under reduced pressure to give yellow oil. The yellow oil was dissolved in 50 ml anhydrous toluene, added with potassium carbonate (20 mmol), and reacted at 110° C. overnight. After being cooled to room temperature, the system was quenched by adding saturated aqueous solution of ammonium chloride, and extracted with dichloromethane. The organic phase separated was washed with saturated brine, and dried with anhydrous sodium sulfate and with rotary evaporation to give white solid with a yield of 90%.

Example 4

Synthesis of (R)-1-(1-phenylethyl)-7-methyl-1,4-diazepane-2,5-dione

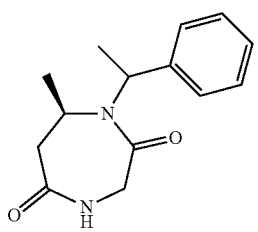 [SMILES: CC(c1ccccc1)N1C(=O)CNC(=O)C[C@H]1C]

(R)-methyl 3-(N-(1-phenylethyl)-2-((t-butyloxycarboryl) amino)acetamido) butyrate (10 mmol) was added into a flask, dissolved with 10 ml methanol; added with 40 ml of 30 mass % of solution of HCl in methanol, and reacted at 50° C. for 6 h. The mixture was concentrated to dry under reduced pressure to give yellow oil. The system was dissolved in 50 ml anhydrous toluene, added with sodium hydride (40 mmol), and reacted at 110° C. overnight. After being cooled to room temperature, the system was quenched by adding saturated aqueous solution of ammonium chloride, and extracted with dichloromethane. The organic phase separated was washed with saturated brine, and dried with anhydrous sodium sulfate and with rotary evaporation to give white solid with a yield of 85%.

Example 5

Synthesis of (R)-1-(4-methoxybenzyl)-7-methyl-1,4-diazepane-2,5-dione

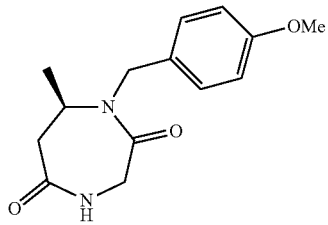 [SMILES: COc1ccc(CN2C(=O)CNC(=O)C[C@H]2C)cc1]

(R)-methyl 3-(N-(4-methoxybenzyl)-2-((t-butyloxycarboryl)amino)acetamido)butyrate (10 mmol) was added into a flask, dissolved with 10 ml methanol, added with 40 ml of 30 mass % of solution of HCl in methanol, and reacted at 50° C. for 6 h. The mixture was concentrated to dry under reduced pressure to give yellow oil. The yellow oil was dissolved in 50 ml anhydrous toluene, added with sodium carbonate (20 mmol), and reacted at 110° C. overnight. After being cooled to room temperature, the system was quenched by adding saturated aqueous solution of ammonium chloride, and extracted with dichloromethane. The organic phase separated was washed with saturated brine, and dried with anhydrous sodium sulfate and with rotary evaporation to give white solid with a yield of 85%.

Example 6

Synthesis of (R)-1-(4-chlorobenzyl)-7-methyl-1,4-diazepane-2,5-dione

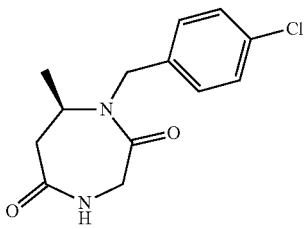 [SMILES: C[C@@H]1CC(=O)NCC(=O)N1Cc1ccc(Cl)cc1]

(R)-methyl 3-(N-(4-chlorobenzyl)-2-((t-butyloxycarboryl)amino)acetamido) butyrate (10 mmol) was added into a flask, dissolved with 10 ml methanol, added with 40 ml of 30 mass % of solution of HCl in methanol, and reacted at 50° C. for 6 h. The mixture was concentrated to dry under reduced pressure to give yellow oil. The yellow oil was dissolved in 50 ml anhydrous toluene, added with potassium t-butoxide (40 mmol), and reacted at 110° C. overnight. After being cooled to room temperature, the system was quenched by adding saturated aqueous solution of ammonium chloride, and extracted with dichloromethane. The organic phase separated was washed with saturated brine, and dried with anhydrous sodium sulfate and with rotary evaporation to give white solid with a yield of 88%.

Example 7

Synthesis of (R)-1-(3-fluorobenzyl)-7-methyl-1,4-diazepane-2,5-dione

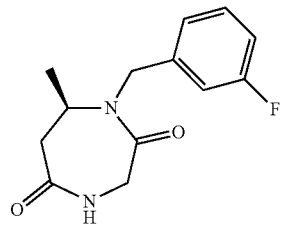 [SMILES: C[C@@H]1CC(=O)NCC(=O)N1Cc1cccc(F)c1]

(R)-methyl-3-(N-(3-fluorobenzyl)-2-((t-butyloxycarboryl)amino)acetamido)butyrate (10 mmol) was added into a flask, dissolved with 10 ml methanol, added with 40 ml of 30 mass % of solution of HCl in methanol, and reacted at 50° C. for 6 h. The mixture was concentrated to dry under reduced pressure to give yellow oil. The yellow oil was dissolved in 50 ml anhydrous toluene, added with triethylamine (40 mmol), and reacted at 80° C. overnight. After being cooled to room temperature, the system was quenched by adding saturated aqueous solution of ammonium chloride, and extracted with dichloromethane. The organic phase separated was washed with saturated brine, and dried with anhydrous sodium sulfate and with rotary evaporation to give white solid with a yield of 80%.

Example 8

Synthesis of (R)-1-(2-methylbenzyl)-7-methyl-1,4-diazepane-2,5-dione

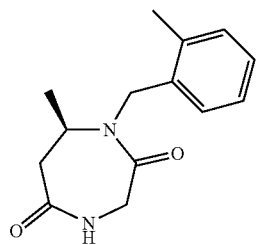 [SMILES: Cc1ccccc1CN1C(=O)CNC(=O)C[C@H]1C]

(R)-methyl 3-(N-(2-methylbenzyl)-2-((t-butyloxycarboryl)amino)acetamido) butyrate (10 mmol) was added into a flask, dissolved with 10 ml methanol, added with 40 ml of 30 mass % of solution of HCl in methanol, and reacted at 50° C. for 6 h. The mixture was concentrated to dry under reduced pressure to give yellow oil. The yellow oil was dissolved in 50 ml anhydrous toluene, added with potassium carbonate (20 mmol), and reacted at 110° C. overnight. After being cooled to room temperature, the system was quenched by adding saturated aqueous solution of ammonium chloride, and extracted with dichloromethane. The organic phase separated was washed with saturated brine, and dried with anhydrous sodium sulfate and with rotary evaporation to give white solid in a yield of 93%.

Example 9

Synthesis of (R)-1-(4-nitrobenzyl)-7-methyl-1,4-diazepane-2,5-dione

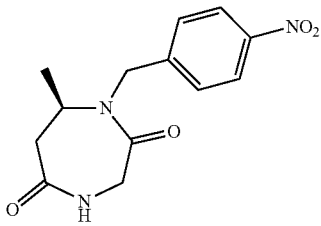 [SMILES: C[C@@H]1CC(=O)NCC(=O)N1Cc1ccc([N+](=O)[O-])cc1]

(R)-methyl 3-(N-(4-nitrobenzyl)-2-((t-butyloxycarboryl)amino)acetamido) butyrate (10 mmol) was added into a flask, dissolved with 10 ml methanol, added with 40 ml of 30 mass % of solution of HCl in methanol, and reacted at 50° C. for 6 h. The mixture was concentrated to dry under reduced pressure to give yellow oil. The yellow oil was dissolved in 50 ml anhydrous toluene, added with potassium carbonate (20 mmol), and reacted at 110° C. overnight. After being cooled to room temperature, the system was quenched by adding saturated aqueous solution of ammonium chloride, and extracted with dichloromethane. The organic phase separated was washed with saturated brine, and dried with anhydrous sodium sulfate and with rotary evaporation to give white solid with a yield of 89%.

Example 10

Synthesis of (R)-1-benzyl-7-methyl-1,4-diazepane-2,5-dione (R)-methyl 3-(N-benzyl-2-((t-butyloxycarboryl)amino)acetamido)butyrate (10 mmol) was added into a flask, dissolved with 10 ml ethyl acetate, added with 40 ml of 45 mass % ethyl acetate hydrochloric acid solution, and reacted at 50° C. for 6 h. The mixture was concentrated to dry under reduced pressure to give yellow oil. The yellow oil was dissolved in 50 ml anhydrous methanol, added with sodium methylate (15 mmol), and reacted at 110° C. under nitrogen overnight. The system was quenched with saturated aqueous solution of ammonium chloride, and extracted with dichloromethane. The organic phase separated was washed with saturated brine, and dried with anhydrous sodium sulfate and with rotary evaporation to give white solid with a yield of 94%.

Example 11

Synthesis of (R)-1-benzyl-7-methyl-1,4-diazepane-2,5-dione (R)-methyl 3-(N-benzyl-2-((t-butyloxycarboryl)amino) acetamido) butyrate (10 mmol) was added into a flask, dissolved with 10 ml dichloromethane, added with 40 ml solution of 20 mass % trifluoroacetic acid in dichloromethane, and reacted at 25° C. for 6 h. The mixture was concentrated to dry under reduced pressure to give yellow oil. The yellow oil was dissolved in 50 ml anhydrous toluene, added with sodium hydride (15 mmol), and reacted at 110° C. under nitrogen atmosphere overnight. The system was quenched with saturated aqueous solution of ammonium chloride, and extracted with dichloromethane. The organic phase separated was washed with saturated brine, and dried with anhydrous sodium sulfate and with rotary evaporation to give white solid with a yield of 91%.

Example 12

Synthesis of (R)-1-benzyl-7-methyl-1,4-diazepane-2,5-dione (R)-methyl 3-(N-benzyl-2-((t-butyloxycarboryl)amino) acetamido)butyrate (10 mmol) was added into a flask, dissolved with 10 ml methanol, added with 40 ml of 30 mass % of solution of HCl in methanol, and reacted at 50° C. for 6 h. The mixture was concentrated to dry under reduced pressure to give yellow oil. The yellow oil was dissolved in 50 ml anhydrous methanol, added with triethylamine (30 mmol), and reacted at 60° C. under nitrogen atmosphere overnight. The system was quenched with saturated aqueous solution of ammonium chloride, and extracted with dichloromethane. The organic phase separated was washed with saturated brine, and dried with anhydrous sodium sulfate and with rotary evaporation to give white solid with a yield of 90%.

Example 13

Synthesis of (R)-1-benzyl-7-methyl-1,4-diazepane

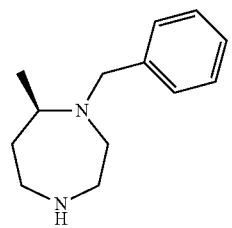

(R)-1-benzyl-7-methyl-1,4-diazepan-2,5-dione (10 mmol) was dissolved in 30 ml anhydrous tetrahydrofuran, which was added to 30 ml anhydrous tetrahydrofuran containing 2 g sodium borohydride (54 mmol) under an ice-water bath, added dropwise with 24 mmol iodine dissolved in 40 ml anhydrous tetrahydrofuran under nitrogen atmosphere, and refluxed overnight. After being cooled to 0° C., the system was quenched by adding 15 ml of 2M HCl solution, then added with 20 ml of 3M sodium hydroxide solution. The mixture was separated, and the aqueous phase was extracted twice with dichloromethane. The organic phases were combined, washed with saturated brine, and dried with anhydrous sodium sulfate. After suction filtration, the solvent was removed under reduced pressure to give colorless oily liquid with a yield of 89%. $^1$H NMR (400 MHz, CDCl$_3$) δ 7.31-7.15 (m, 5H), 3.74-3.56 (m, 3H), 3.29 (t, J=6.6 Hz, 2H), 3.04-2.94 (m, 2H), 2.85-2.76 (m, 1H), 2.59 (dd, J=15.5, 3.3 Hz, 1H), 2.23-2.11 (m, 1H), 1.92-1.80 (m, 1H), 1.02 (d, J=6.3 Hz, 3H); MS (ESI) m/z 205.10 ([M+H]$^+$).

Example 14

Synthesis of (R)-1-benzyl-7-methyl-1,4-diazepane (R)-1-benzyl-7-methyl-1,4-diazepan-2,5-dione (10 mmol) was dissolved in 100 ml anhydrous tetrahydrofuran, added portionwise with lithium aluminum hydride (60 mmol) under an ice-water bath, and stirred at 25° C. overnight. After being cooled to −5° C., the system was quenched by adding 2 ml ice water, then added with 20 ml of 3M sodium hydroxide solution. The mixture was separated, and the aqueous phase was extracted twice with dichloromethane. The organic phases were combined, washed with saturated brine, and dried with anhydrous sodium sulfate. After suction filtration, solution was removed under reduced pressure to give colorless oily liquid with a yield of 90%.

Example 15

Synthesis of (R)-1-benzyl-7-methyl-1,4-diazepane (R)-1-benzyl-7-methyl-1,4-diazepan-2,5-dione (10 mmol) was dissolved in 100 ml anhydrous tetrahydrofuran, added dropwise with borane dimethyl sulfide solution (20 mmol) under an ice-water bath, stirred at 65° C. overnight. After being cooled to −5° C., the system was quenched by adding 2 ml methanol, adjusted to pH 3, further stirred for 3 h, adjusted to pH 10 with sodium carbonate. The aqueous phase separated was extracted three times with dichloromethane; the resulted organic phases were combined, washed with saturated brine, and dried with anhydrous sodium sulfate. After suction filtration, solution was removed under reduced pressure to give colorless oily liquid in a yield of 87%.

Example 16

Synthesis of 5-chloro-2-[(5R)-hexahydro-4-benzyl-5-methyl-1H-1,4-diazepin-1-yl]benzoxazole

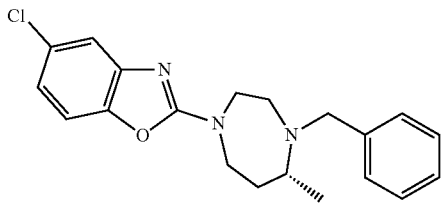 [SMILES: C[C@H]1CCN(c2nc3cc(Cl)ccc3o2)CCN1Cc1ccccc1]

A solution of (R)-1-benzyl-7-methyl-1,4-diazepane (10 mmol) in 40 ml DMF was added with 2,5-dichlorobenzoxazole (10 mmol) and triethylamine (25 mmol), and the mixture was heated to 75° C. to react for 3 h. After being cooled to room temperature, the system was added with saturated aqueous solution of sodium hydrogencarbonate, and the aqueous phase separated was extracted with ethyl acetate. The resulted organic phase was washed with saturated brine, dried with anhydrous sodium sulfate, suction filtrated, concentrated under reduced pressure to give colorless oily liquid with a yield of 95%. $^1$H NMR (400 MHz, cdcl$_3$) δ 7.40-7.25 (m, 5H), 7.23 (dd, J=7.3, 2.2 Hz, 1H), 7.12 (d, J=8.4 Hz, 1H), 6.94 (dd, J=8.4, 2.1 Hz, 1H), 3.92-3.82 (m, 2H), 3.76-3.56 (m, 4H), 3.13 (ddd, J=8.1, 6.8, 3.9 Hz, 1H), 2.96 (ddd, J=14.6, 6.9, 3.1 Hz, 1H), 2.81 (ddd, J=14.6, 7.4, 3.2 Hz, 1H), 2.20-2.11 (m, 1H), 1.84-1.76 (m, 1H), 1.13 (d, J=6.7 Hz, 3H); MS (ESI) m/z 356.10 ([M+H]$^+$).

Example 17

Synthesis of 5-chloro-2-[(5R)-hexahydro-4-benzyl-5-methyl-1H-1,4-diazepin-1-yl]benzoxazole A solution of (R)-1-benzyl-7-methyl-1,4-diazepane (10 mmol) in 40 ml DMF was added with 2,5-dichlorobenzoxazole (10 mmol) and potassium carbonate (25 mmol), and heated to 75° C. to react for 3 h. After being cooled to room temperature, the system was added with water, and the aqueous phase separated was extracted with ethyl acetate. The resulted organic phase was washed with saturated brine, dried with anhydrous sodium sulfate, suction filtrated, and concentrated under reduced pressure to give colorless oily liquid with a yield of 89%.

Example 18

Synthesis of 5-chloro-2-[(5R)-hexahydro-4-benzyl-5-methyl-1H-1,4-diazepin-1-yl]benzoxazole A solution of (R)-1-benzyl-7-methyl-1,4-diazepane (10 mmol) in 40 ml THF was added with 2,5-dichlorobenzoxazole (10 mmol) and N-methyl morpholine (25 mmol), and heated to 75° C. to react for 3 h. After being cooled to room temperature, the system was added with water, and the aqueous phase separated was extracted with ethyl acetate. The resulted organic phase was washed with saturated brine, dried with anhydrous sodium sulfate, suction filtrated, and concentrated under reduced pressure to give colorless oily liquid with a yield of 85%.

Example 19

Synthesis of 5-chloro-2-[(5R)-hexahydro-4-benzyl-5-methyl-1H-1,4-diazepin-1-yl]benzoxazole A solution of (R)-1-benzyl-7-methyl-1,4-diazepane (10 mmol) in 40 ml acetonitrile was added with 2,5-dichlorobenzoxazole (10 mmol) and sodium bicarbonate (25 mmol), and heated to 75° C. to react for 3 h. After being cooled to room temperature, the system was added with water, and the aqueous phase separated was extracted with ethyl acetate. The resulted organic phase was washed with saturated brine, dried with anhydrous sodium sulfate, suction filtrated, and concentrated under reduced pressure to give colorless oily liquid in a yield of 75%.

Example 20

Synthesis of 5-chloro-2-[(5R)-hexahydro-5-methyl-1H-1,4-diazepin-1-yl]benzoxazole

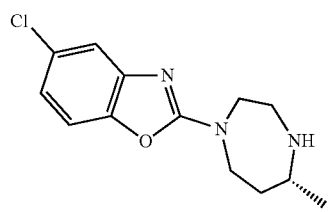 [SMILES: C[C@H]1CCN(c2nc3cc(Cl)ccc3o2)CCN1]

5-chloro-2-[(5R)-hexahydro-4-benzyl-5-methyl-1H-1,4-diazepin-1-yl]benzoxazole (5 mmol) was dissolved in 25 ml 1,2-dichloroethane, cooled to 0 to 5° C. in an ice-water bath, and added with chloroethyl chloroformate (12.5 mmol). The mixture was stirred at this temperature for 1 hour, heated to 80° C. and stirred overnight. The system was cooled to room temperature and concentrated to remove the solvent under reduced pressure, and the residue was dissolved in 25 ml methanol and stirred at 70° C. for 3 h. 5 mass % sodium hydrogencarbonate solution was added, and then the mixture was extracted twice with dichloromethane. The resulted organic phase was dried with anhydrous sodium sulfate, suction filtrated, and concentrated under reduced pressure to give oily liquid with a yield of 92%. MS (ESI) m/z 266.10 ([M+H]$^+$).

Example 21

Synthesis of 5-chloro-2-[(5R)-hexahydro-5-methyl-1H-1,4-diazepin-1-yl]benzoxazole 5-chloro-2-[(5R)-hexahydro-4-benzyl-5-methyl-1H-1,4-diazepin-1-yl]benzoxazole (5 mmol) was dissolved in 50 ml ethyl acetate, added with 10 mass % Pd/C (0.1M); the air in the system was replaced with hydrogen three times to allow a reaction at 50° C. overnight. The system was cooled to room temperature, suction filtrated, and concentrated under reduced pressure to give oily liquid with a yield of 45%. MS (ESI) m/z 266.10 ([M+H]$^+$).

Example 22

Synthesis of Suvorexant

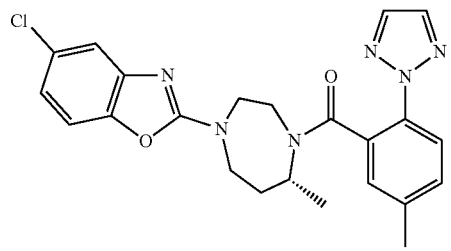 [SMILES: Cc1ccc(-n2nccn2)c(C(=O)N2CCN(c3nc4cc(Cl)ccc4o3)CC[C@@H]2C)c1]

5-chloro-2-[(5R)-hexahydro-5-methyl-1H-1,4-diazepin-1-yl]benzoxazole (10 mmol) was dissolved in 50 ml anhydrous DMF, cooled to 0 to 5° C., and added with 1-hydroxybenzotriazole (11 mmol), 1-ethyl-(3-dimethylaminopropyl)carbodiimide hydrochloride (11 mmol), anhydrous ethylamine (25 mmol) and 5-methyl-2-(2H-1,2,3-triazol-2-yl)benzoic acid (10.5 mmol) with stirring; then the mixture were heated to 50° C. and reacted for 6 h. 10 mass % citric acid solution was added, and the aqueous phase separated was extracted with ethyl acetate. The resulted organic phase was washed successively with saturated solution of sodium hydrogen carbonate and saturated brine, dried over anhydrous sodium sulfate, filtrated and dried by evaporation. The resulted product was recrystallized with isopropyl acetate and n-heptane to give suvorexant with a yield of 83%, and the ee value is 99.9%. m.p.: 128-129° C., MS (ESI) m/z 451.20 ([M+H]$^+$).

Example 23

Synthesis of Suvorexant 5-chloro-2-[(5R)-hexahydro-5-methyl-1H-1,4-diazepin-1-yl]benzoxazole (75 mmol) was dissolved in N,N-Dimethylformamide (75 ml), then cooled to 0 to 5° C., and added with 5-methyl-2-(2H-1,2,3-triazole-2-yl)benzoic acid (79 mmol), HOAt (82.8 mmol), EDCI (82.8 mmol) and triethylamine (188 mmol); then the mixture was warmed naturally and stirred at room temperature overnight. 10 mass % citric acid solution was added, and the aqueous phase separated was extracted with ethyl acetate. The resulted organic phase was washed with 5% sodium carbonate solution and saturated brine, dried over anhydrous sodium sulfate, filtrated and dried by evaporation, to give suvorexant with a yield of 97%, and the ee value is 99.8%.

Example 24

Synthesis of Suvorexant 5-chloro-2-[(5R)-hexahydro-5-methyl-1H-1,4-diazepin-1-yl]benzoxazole (75 mmol) was dissolved in THF (75 ml), then cooled to 0 to 5° C., and added with 5-methyl-2-(2H-1,2,3-triazole-2-yl)benzoic acid (79 mmol), HOBt (82.8 mmol), EDCI (82.8 mmol) and triethylamine (188 mmol); then the mixture was warmed naturally and stirred at room temperature overnight. 10 mass % citric acid solution was added, and the aqueous phase separated was extracted with ethyl acetate. The resulted organic phase was washed with 5 mass % sodium carbonate solution and saturated brine, dried over anhydrous sodium sulfate, filtrated and dried by evaporation, to give suvorexant with a yield of 92%, and the ee value is 99.9%.

Example 25

Synthesis of Suvorexant 5-chloro-2-[(5R)-hexahydro-5-methyl-1H-1,4-diazepin-1-yl]benzoxazole (75 mmol) was dissolved in dichloromethane (75 ml); then cooled to 0 to 5° C., and added with 5-methyl-2-(2H-1,2,3-triazole-2-yl)benzoic acid (79 mmol), HOBt (82.8 mmol), EDCI (82.8 mmol) and triethylamine (188 mmol); then the mixture was warmed naturally and stirred at room temperature overnight. 10% citric acid solution was added, and the aqueous phase separated was extracted with ethyl acetate. The resulted organic phase was washed with 5% sodium carbonate solution and saturated brine, dried over anhydrous sodium sulfate, filtrated and dried by evaporation, to give suvorexant with a yield of 93%, and the ee value is 99.9%.

The invention claimed is:

1. A method for preparing a compound of formula VI, comprising:
deprotecting a protecting group R from a compound of formula V via a deprotection reaction in the presence of a catalyst in an organic solvent,

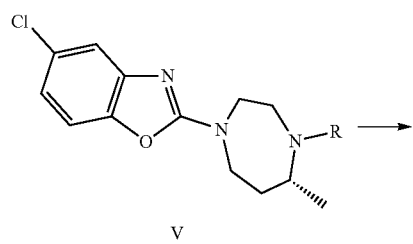

V

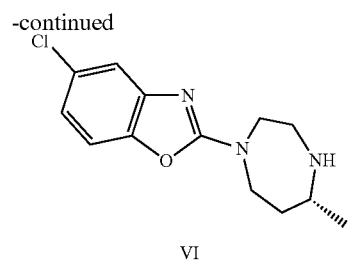

VI wherein, R represents benzyl, allyl, 1-phenethyl, or optionally substituted benzyl at the 2 position to 6 position.

2. The method according to claim 1, wherein, the organic solvent used in the deprotection reaction is selected from the group consisting of a $C_1$-$C_4$ lower alcohol and a halohydrocarbon; and the catalyst used in the deprotection reaction is selected from the group consisting of a chloroformate catalyst and a palladium catalyst.

3. The method according to claim 1, further comprising preparing the compound of formula V, comprising:

subjecting a compound of formula IV and 2,5-dichlorobenzoxazole to a C—N coupling reaction in the presence of an alkali, to give the compound of formula V or a salt thereof,

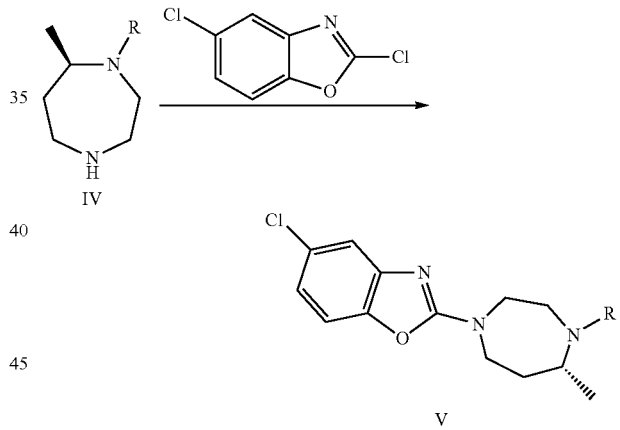

wherein, R represents benzyl, allyl, 1-phenethyl, or optionally substituted benzyl at the 2 position to 6 position.

4. The method according to claim 3, wherein a solvent used in the C—N coupling reaction is selected from the group consisting of N,N-dimethylformamide, toluene, tetrahydrofuran and acetonitrile; and the alkali used in the C—N coupling reaction is selected from the group consisting of triethylamine, N-methylmorpholine, piperidine, N-methylpiperazine, sodium hydrogencarbonate, potassium carbonate, sodium carbonate, and sodium hydride.

5. The method according to claim 3, further comprising preparing the compound of formula IV, comprising:

reducing a compound of formula III via a reduction reaction in the presence of a reducing agent, to give the compound of formula IV, or a salt thereof,

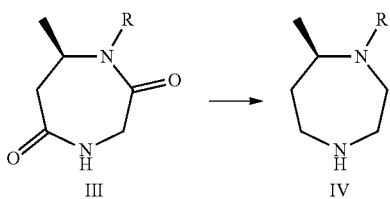

wherein, R is defined as that of claim 1.

6. The method according to claim 5, wherein a solvent used in the reduction reaction is selected from the group consisting of dichloromethane and tetrahydrofuran; and
the reducing agent used in the reduction reaction is selected from the group consisting of borane, sodium borohydride, lithium borohydride, sodium cyanoborohydride, lithium aluminum hydride, and sodium hydride.

7. The method according to claim 5, further comprising preparing the compound of formula III, comprising:
deprotecting t-butoxycarbonyl from a compound of formula II in the presence of an acid in an organic solvent, to give a corresponding amine or a salt thereof; and
subjecting the corresponding amine or the salt thereof to a cyclization reaction in the presence of an alkali to give the compound of formula III;

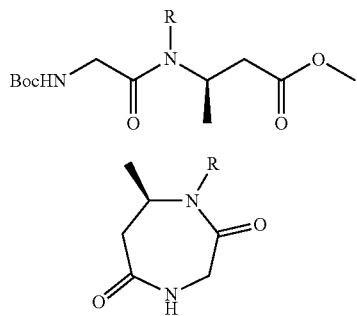

wherein, R represents benzyl, allyl, 1-phenethyl, or optionally substituted benzyl at the 2 position to 6 position.

8. The method according to claim 7, wherein the organic solvent used in the reaction of deprotecting the t-butoxycarbonyl from the compound of formula II is selected from the group consisting of ethyl acetate, dichloromethane, N,N-dimethylformamide, acetonitrile, toluene, methanol, and ethanol;
wherein the acid used in the reaction of deprotecting the t-butoxycarbonyl from the compound of formula II is selected from the group consisting of HCl and trifluoroacetic acid; and wherein the alkali in the reaction of deprotecting the t-butoxycarbonyl from the compound of formula II is selected from the group consisting of magnesium alkoxide, sodium alkoxide, sodium hydride, sodium hydrogencarbonate, sodium carbonate, potassium carbonate, sodium borohydride, potassium t-butoxide, and triethylamine.

9. The method according to claim 7, further comprising preparing the compound of formula II, comprising:
subjecting a compound of formula I and glycine protected by Boc to a condensation reaction in the presence of a condensation agent in an organic solvent, to obtain the compound of formula II;

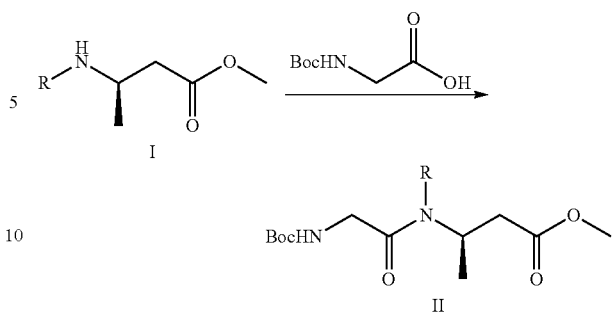

wherein, R represents benzyl, allyl, 1-phenethyl, or optionally substituted benzyl at the 2 position to 6 position.

10. The method according to claim 9, wherein the organic solvent used in the condensation reaction for preparing the compound of formula II is selected from the group consisting of dichloromethane, tetrahydrofuran, and N,N-dimethylformamide; an alkali used in the condensation reaction for preparing the compound of formula II is selected from the group consisting of triethylamine, 1,8-diazabicyclo (5.4.0) undec-7-ene (DBU), 4-dimethylaminopyridine (DMAP), N-methylmorpholine, N-methylpiperazine, piperidine, sodium hydrogencarbonate, and potassium carbonate; and
the condensation agent used in the condensation reaction for preparing the compound of formula II is selected from the group consisting of 1-ethyl-(3-dimethyl aminopropyl)carbodiimide hydrochloride, N,N'-carbonyldiimidazole, dicyclohexylcarbodiimide, 1-hydroxybenzotriazole, and 1-hydroxy-7-azobenzotriazole.

11. A method for preparing suvorexant, comprising:
providing a compound of formula VI prepared by the method according to claim 1; and
subjecting the compound of formula VI and 5-methyl-2-(2H-1,2,3-triazol-2-yl)benzoic acid to a condensation reaction in the presence of a condensation agent, an alkali and an aprotic solvent, to give suvorexant, shown as the following reaction formula:

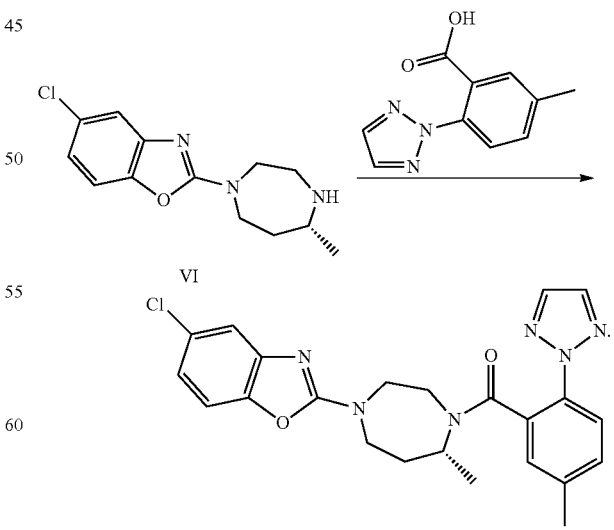

12. The method according to claim 11, wherein the aprotic solvent used in the condensation reaction for preparing suvorexant is selected from the group consisting of acetonitrile, tetrahydrofuran, toluene, dichloromethane, and N,N-dimethylformamide;
the condensation agent used in the condensation reaction for preparing suvorexant is selected from the group consisting of 1-ethyl-3-(3-dimethylaminopropyl)carbodiimide hydrochloride, N,N-diisopropylcarbodiimide, N,N'-carbonyldiimidazole, dicyclohexylcarbodiimide, 1-hydroxybenzotriazole, and 1-hydroxy-7-azobenzotriazole; and
the alkali used in the condensation reaction for preparing suvorexant is selected from the group consisting of triethylamine, 1,8-diazabicyclo (5.4.0) undec-7-ene, 4-dimethylaminopyridine, N-methylmorpholine, N-methylpiperazine and piperidine.

13. The method according to claim 2, wherein, the organic solvent is selected from the group consisting of methanol, ethanol and 1,2-dichloroethane, and/or the catalyst is selected from the group consisting of chloroethyl chloroformate, Pd/C, Pd(OH)$_2$/C and PdCl$_2$/C.

14. The method according to claim 1, wherein, the optionally substituted benzyl at the 2 position to 6 position is selected from the group consisting of 4-methoxybenzyl, 4-nitrobenzyl, 2-methylbenzyl, 4-chlorobenzyl and 3-fluorobenzyl.

15. The method according to claim 10, wherein, the alkali is triethylamine or N-methylmorpholine; and/or the condensation agent is a combination of 1-hydroxybenzotriazole and 1-ethyl-(3-dimethylaminopropyl)carbodiimide hydrochloride.

16. The method according to claim 12, wherein, the aprotic solvent is N,N-dimethylformamide; the alkali is triethylamine or N-methylmorpholine; and/or the condensation agent is a combination of 1-hydroxybenzotriazole and 1-ethyl-(3-dimethylaminopropyl)carbodiimide hydrochloride.

17. A method for preparing suvorexant, comprising using a compound of formula II, a compound of formula III, a compound of formula IV, or a compound of formula V, or salts thereof,

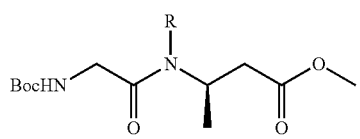
II

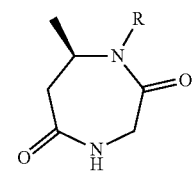
III

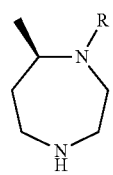
IV

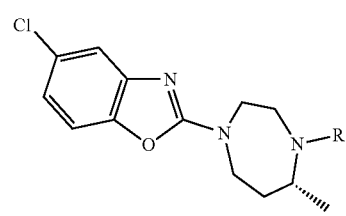
V wherein, R represents benzyl, allyl, 1-phenethyl, or optionally substituted benzyl at the 2 position to 6 position.

* * * * *